United States Patent
Nakahara et al.

[11] Patent Number: 5,837,886
[45] Date of Patent: Nov. 17, 1998

[54] GAS SENSOR

[75] Inventors: Takeshi Nakahara, Osaka; Tomohiro Inoue, Hyogo; Hironobu Machida, Osaka, all of Japan

[73] Assignee: Figaro Engineering Inc., Osaka, Japan

[21] Appl. No.: 884,507

[22] Filed: Jun. 27, 1997

Related U.S. Application Data

[63] Continuation of Ser. No. 610,880, Mar. 5, 1996, abandoned.

[30] Foreign Application Priority Data

Jun. 19, 1995 [JP] Japan ................................ 7-176620

[51] Int. Cl.$^6$ .............................. G01N 7/00; H01R 9/09; H01C 7/00
[52] U.S. Cl. .......................... 73/31.06; 174/262; 338/34
[58] Field of Search .......................... 73/31.06; 174/262; 338/34

[56] References Cited

U.S. PATENT DOCUMENTS

| | | | |
|---|---|---|---|
| 3,676,820 | 7/1972 | Taguchi | 338/34 |
| 3,906,473 | 9/1975 | Le Vine | 340/237 R |
| 4,221,827 | 9/1980 | Parry et al. | 427/125 |
| 4,224,280 | 9/1980 | Takahama et al. | 422/98 |
| 4,237,722 | 12/1980 | Achari | 73/23 |
| 4,396,899 | 8/1983 | Ohno | 338/34 |
| 4,399,424 | 8/1983 | Rigby | 338/34 |
| 4,399,684 | 8/1983 | Advani et al. | 73/1 G |
| 4,580,439 | 4/1986 | Manaka | 73/31.06 |
| 4,596,975 | 6/1986 | Reddy et al. | |
| 4,816,800 | 3/1989 | Onaga et al. | 338/34 |
| 4,938,928 | 7/1990 | Koda et al. | 422/98 |
| 4,967,589 | 11/1990 | Yagawara et al. | 73/23.25 |
| 4,984,446 | 1/1991 | Yagawara et al. | 73/31.06 |
| 5,012,671 | 5/1991 | Yagawara et al. | 73/31.06 |
| 5,389,225 | 2/1995 | Aagard et al. | 204/426 |
| 5,400,643 | 3/1995 | De Angelis et al. | 73/31.06 |
| 5,455,390 | 10/1995 | DiStefano et al. | 174/262 |
| 5,466,605 | 11/1995 | Glausinger et al. | 436/6 |

FOREIGN PATENT DOCUMENTS

| | | |
|---|---|---|
| 0 014 087 A1 | 8/1980 | European Pat. Off. |
| 60-209161 | 10/1985 | Japan |
| 3-130654 | 6/1991 | Japan |
| 2 085 168 | 4/1982 | United Kingdom |

*Primary Examiner*—Herzon E. Williams
*Assistant Examiner*—Jay L. Politzer
*Attorney, Agent, or Firm*—Nikaido, Marmelstein, Murray & Oram LLP

[57] ABSTRACT

A film heater and thick-film electrode pads are provided on one main surface of a heat-resistant insulating substrate and are connected by through holes to a metal oxide semiconductor film on the tail surface. Pads are made of a gold alloy such as Au—Pt and connected to leads of Pt—W, etc.

6 Claims, 7 Drawing Sheets

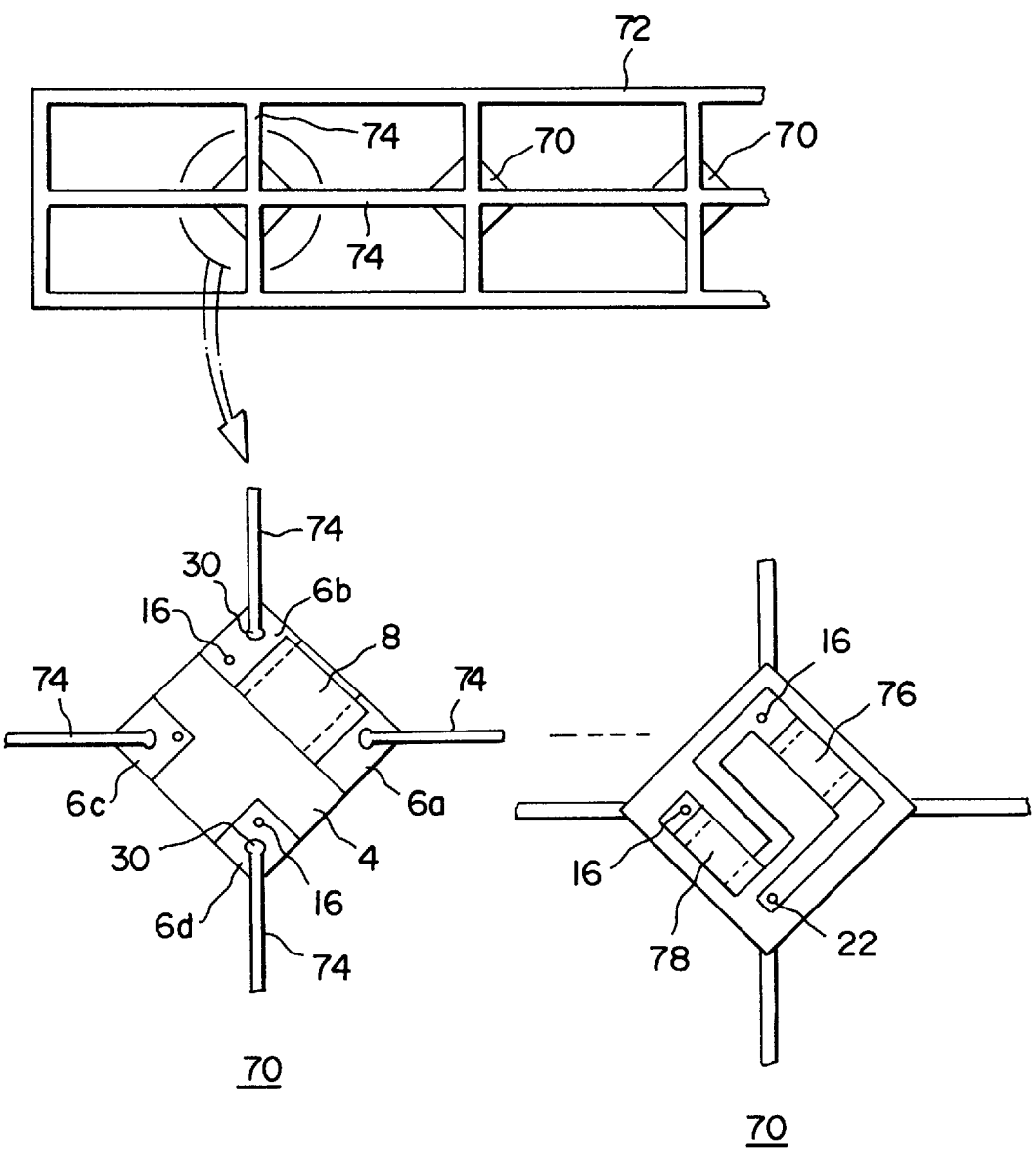

GAS SENSOR

This application is a continuation of application Ser. No. 08/610,880 filed Mar. 5, 1996 now abandoned.

FIELD OF THE INVENTION

The present invention relates to improvement of metal oxide semi-conductor gas sensor, and in particular, it relates to the connection of the sensor element to external terminals.

PRIOR ART

One major requirement for metal oxide semiconductor gas sensors is to reduce its power consumption, and in turn, to reduce the cost of the power source circuit required to drive a gas sensor. To this end, it is necessary to miniaturize the gas sensor by using printing technology and thin film technology and to reduce the heat conduction of the leads used for the gas sensor. The leads account for the greater part of the heat release from the gas sensor. To reduce its power consumption, it is necessary to use for the leads a material of which thermal conductivity is low, and to reduce the wire diameter of the leads.

An application of the metal oxide semiconductor gas sensor, which is attracting much attention now, is the detection of carbon monoxide (CO). In this case, the temperature of the gas sensor is made to change cyclically. The metal oxide semiconductor of the gas sensor is subjected to heat cleaning by heating it to high temperatures. At the low temperature side, the output of the metal oxide semiconductor film exhibits a selectivity to CO. This property is used to detect CO. This means the gas sensor is constantly exposed to thermal shocks.

The present inventors faced the following problems in the course of development of a gas sensor which has a small power consumption and is suitable for the detection of CO:

1) When pure gold was used for the thick-film electrode pads to which leads are to be connected, the pads came off from the substrate due to repeated temperature changes;
2) When platinum was used for the thick-film electrode pads to avoid the above-mentioned problem, it was difficult to connect the leads to the pads; and
3) It was difficult to connect Pt—W wire (Pt—W alloy wire) and APM wire (Au—Pd—Mo alloy wire), which are suitable for leads because of their small power consumption, to the pads, and the platinum pads did not show a satisfactory bonding strength.

To produce a gas sensor of which power consumption is small and which has a high durability against temperature changes, it, therefore, is necessary to have thick-film electrode pads which have a high adhesion to the substrate and excel in connection with leads.

Let us examine here related prior arts. Japanese provisional patent publication HEI-3-130654 discloses the following gas sensor. On one main surface of a virtually square substrate, a metal oxide semiconductor film is arranged. On the other main surface of the substrate, a film heater is arranged. Electrodes connecting to the metal oxide semiconductor film are led via through holes to the film heater side, and thick-film electrode pads of platinum are connected to the film heater and the metal oxide semiconductor film. Then leads are connected to these electrode pads by thermocompression bonding. As a result, all the electrode pads are arranged on the film heater side, and both the main surfaces of the substrate are connected to each other by the through holes. However, the electrode pads are made of platinum and it is difficult to connect leads having a high resistance and a low thermal conductivity, such as Pt—W wire and APM wire. Thus the reduction in power consumption is rather limited.

Another prior art is Japanese provisional patent publication SHO-60-209161 which discloses the use of thick-film platinum electrode pads for connecting leads to a ZrO2 oxygen sensor; Pt leads are connected by thermocompression bonding or spot welding, and the welding portions are covered by platinum paste. With this arrangement, the deficiency in the bonding strength between the platinum pads and the platinum leads may be improved by the overcoat of the platinum paste. This patent, however, does not provide a pad material which excels in both the adhesion to the substrate and the connection performance with the leads. The overcoat of platinum paste also poses a problem in the case of metal oxide semiconductor gas sensor. Baking of platinum paste requires a temperature of about 900° C. This temperature is higher than the maximum baking temperature (normally from 600° to 700° C.) of metal oxide semiconductors for gas detection, and will degrade the metal oxide semiconductor. Furthermore, both the prior arts do not suggest that when a gas sensor is exposed to repeated temperature changes the adhesion between the pads and the substrate poses a serious problem.

SUMMARY OF THE INVENTION

The object of the present invention is to improve the gas sensor in both the durability against dropping, vibration, etc. and the durability against repeated temperature changes.

Another object of the present invention is to reduce the power consumption of the gas sensor. Still another object of the invention is to achieve an easy connection of leads to the gas sensor.

The gas sensor according to the present invention comprises a heat-resistant insulating substrate; a metal oxide semiconductor film that changes its electrical resistance according to the presence of a gas, a film heater and a plurality of thick-film electrode pads, each provided on the heat-resistant insulating substrate; and leads, wherein said metal oxide semiconductor film, said film heater and leads are connected to said plurality of thick-film electrode pads, and is characterized in that said plurality of thick-film electrode pads are made of an alloy containing gold.

The substrate is a heat-resistant insulating one made of, for example, alumina, silicon or ZrO2. The shape of the substrate may be, for example, square or rectangular. A metal oxide semiconductor film, a film heater and thick-film electrode are arranged on the substrate. The metal oxide semiconductor film and the film heater may be a thin film or a thick film, but the electrode pads are thick films. The reason is that thin-film pads have insufficient adhesion between the pads and the substrate; the pads may easily come off at the time of thermocompression bonding or welding of leads. The film thickness of the electrode pads is, for example, from 2 to 50 μm, and preferably from 5 to 20 μm. The material of the electrode pads is an alloy containing gold, such as Au—Pt, Au—Rh and Au—Pd. Such an alloy may be used to form the electrode pads as a single layer. The electrode pads may be formed in two layers, for example, the lower layer is made of platinum, and the upper layer is made of gold. In such pads of two layers, the component of the upper layer and that of the lower layer are mixed to form an alloy. A specially preferable material for electrode pads is an Au—Pt alloy. The electrode pads may be formed of the alloy from the start or they may be formed in a lower layer of platinum and an upper layer of gold initially, then the upper layer and the lower layer may be alloyed to form Au—Pt alloy pads.

Preferably both the main surfaces, top and tail, of the substrate are used, and a metal oxide semiconductor film such as SnO2 film, ZnO film or In2O3 film is arranged on one of the main surfaces, and a film heater of, for example, RuO2 or Pt is arranged on the other main surface. Then thick-film electrode pads are arranged on one of the main surfaces, and this main surface is connected with the other main surface by means of through holes, etc. Instead of through holes, the connection with the other main surface may be accomplished by, for example, a conducting film or films provided on an edge or a side of the substrate. In this way, the surface area of the substrate can be reduced, in turn, the power consumption can be reduced, and the attachment of the leads can be made easier since all leads are provided on one face of the substrate.

To reduce the power consumption of the gas sensor, it is desirable to use a wire of high electrical resistance for the leads. A wire of high resistance generally has a low thermal conductivity. Low conductivity and small diameter wire provides the desired high resistance, which is necessary to decrease power consumption in the sensor rather than in other elements of the circuit. Kinds of desirable wire include, for example, Pt—W wire (W content is from 2 to 12% by weight), APM wire (Pd content is from 10 to 60% by weight, Mo from 1 to 10% by weight, and the balance is gold), Pt-ZGS wire (Pt—ZrO2 alloy wherein ZrO2 is precipitated in the grain boundary of Pt), and Pt—Pd wire (Pd content is from 5 to 60% by weight). They are precious metal alloy wires and Pt—W wire and APM wire are especially preferred.

The method of using the gas sensor is discretionary. The present invention, however, is particularly suitable when the temperature of the gas sensor is made to change periodically. When the temperature of the gas sensor is made to change periodically, the interfaces between the electrode pads and the substrate will be subjected to repeated thermal shocks, and the pads may come off. To cope with this problem, the present invention uses thick-film electrode pads of a gold alloy so as to improve the adhesion between the substrate and the pads and prevent the pads from coming off. The gold alloy pads can be easily connected with leads, and even if a precious metal alloy wire of high resistance, which is rather difficult to connect, a sufficient bonding strength can be accomplished. As the precious metal alloy wire is used, the heat loss through the leads is reduced and, in turn, the power consumption of the gas sensor is reduced.

Next, if the connections between the leads and the thick-film electrode pads are coated by a thick film, the leads can be secured onto the pads by the coating thick film. As a result, the bonding strength between the leads and the pads can be improved. The thick film materials may be, for example, Au, Au—Pt and Au—Rh. The thick film material may be applied, for example, as a paste to the connections, then baked to solidify. To keep the baking temperature low and, in turn, to prevent the metal oxide semiconductor from degrading, it is desirable to use gold, which can be easily baked at a low temperature, as the thick-film coating material. Furthermore, gold is a material that can easily join bind with the pads and leads, and gold is preferred for improving the bonding strength of the leads as well.

The connection between the leads and the thick-film electrode pads is made by welding such as parallel gap welding, fixation with a thick film of gold paste, etc. or thermosonic compression bonding or the like. Parallel gap welding is known in the art as being a configuration where a gap is created by two parallel welding electrodes. The two electrodes are brought into contact with the piece to be welded, such as a wire. Welding current is then passed between the electrodes; since the welding current passes through the wire, the wire is heated sufficiently to fuse the wire onto the pad. When parallel gap welding is compared with thermosonic compression bonding, welding has a better workability. The process of welding itself, however, can not cut off the leads on the pads, and another process is needed to cut off the leads. Fusing is preferably used for this process. When one lead is welded onto two pads on the substrate, a lead portion will remain between the two pads. When a large current for fusing is passed through the lead portion between these pads, the lead portion will be fused by the generated heat. When there are, for example, four electrode pads, these pads will be located at the respective vertexes. First, two leads are arranged crosswise. Each lead is connected to two pads at two diagonal vertexes of the quadrangle. After that, when two lead portions are fused, leads will extend outwardly from the substrate in the form of a cross. The respective leads are virtually parallel to the corresponding diagonals of said quadrangle. As the leads extend from the substrate in the form of a cross, the durability of the gas sensor is improved against vibrations and external forces in various directions.

According to the present invention, a gold alloy is used for the thick-film electrode pads of the gas sensor. As a result, the adhesion between the pads and the substrate is high. Hence the pads will not come off from the substrate even if the gas sensor is exposed repeated temperature changes. The gold alloy pads have a high bonding strength with the leads. Even when a precious metal alloy wire or the like, which has a low thermal conductivity, is used for the leads, the bonding strength of the leads can be kept at a high level. This means the power consumption of the gas sensor can be reduced.

The connection between the leads and the pads may be achieved by welding such as parallel gap welding, thermocompression bonding such as thermosonic compression bonding, or fixation with a protective layer such as a thick film of gold, etc. Preferably, the leads are connected by welding or thermocompression bonding, then the connections are covered by a thick-film protective layer. In this way, the bonding strength between the lead and the pad is improved. Gold is preferable for the protective layer because gold can be easily baked at low temperature and has an excellent adhesion to the leads.

When the leads are connected to the pads by welding or by means of a protective layer, the lead portions can be easily cut off on the pads by fusing. When there are, for example, four electrode pads, if the leads are arranged virtually parallel to the diagonals of a quadrangle connecting the four pads, the directions of the leads will be diverse. The substrate is held by four leads in a plane; the substrate can be held against vibrations and external forces given in various directions. This can be achieved by arranging and connecting the leads along the diagonals of the quadrangle and then fusing the leads.

BRIEF DESCRIPTION OF THE DRAWINGS

FIG. 13 is a diagram showing the production process of a modification of the gas sensor.

EMBODIMENT

Figure 1:
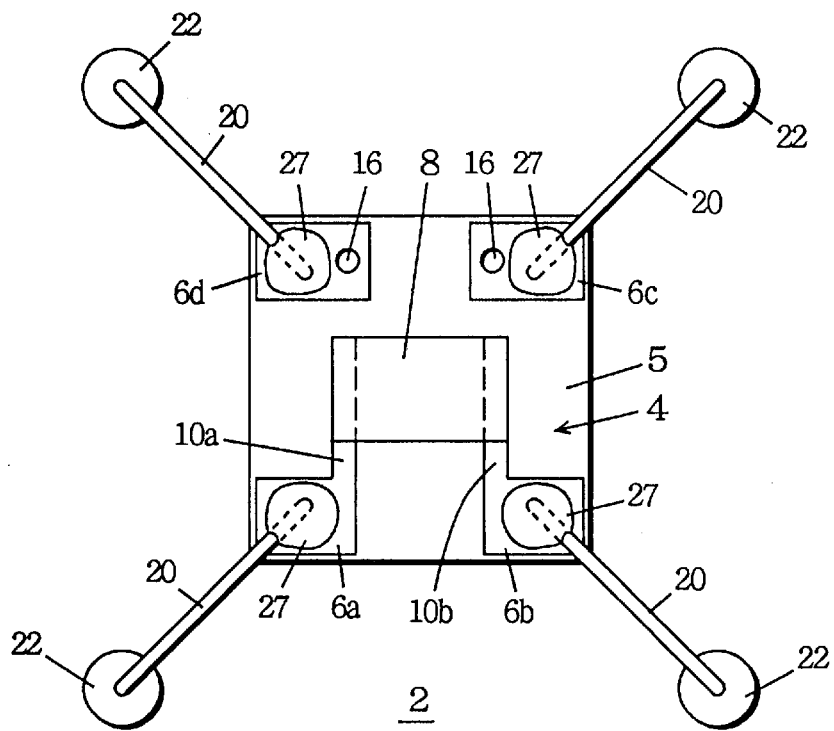
FIG. 1 is a plan view of an essential part of an embodiment of the gas sensor according to the present invention.

FIG. 1 through FIG. 13 show an embodiment and its modifications. The respective modifications are identical to the embodiment except the certain points specified herein. FIG. 1 shows an essential part of the embodiment of the gas sensor. 2 is the sensor element. 4 is a heat-resistant insulating substrate made of, for example, alumina, silicon or ZrO2. 6a through 6d are four thick-film electrode pads. These pads are all arranged on one main surface 5 of the substrate 4. Each electrode pad is made of a gold alloy such as Au—Pt, Au—Rh and Au—Pd. In the embodiment, an Au—Pt alloy is used. The thickness of the electrode pad 6 is, for example, from 2 to 50 $\mu$m, and preferably from 5 to 20 $\mu$m. The latter range of thickness improves the adhesion between the pad and the substrate 4 and can be formed by once or twice of printing. The Au content of the pad 6 is, in average of the four pads 6, from 5 to 95% by weight, and preferably from 20 to 80% by weight; it is taken into consideration that the composition of the pad 6 may vary in the direction of depth. 8 is a film heater made of, for example, an RuO2 film (film thickness is about 10 $\mu$m) or a thin film of pt. In the case of an RuO2 film, an insulating film is provided over its surface by overglazing. Heater electrodes 10a and 10b are connected to the film heater 8. The heater electrodes 10a and 10b are connected to said electrode pads 6a and 6b.

Figure 3:
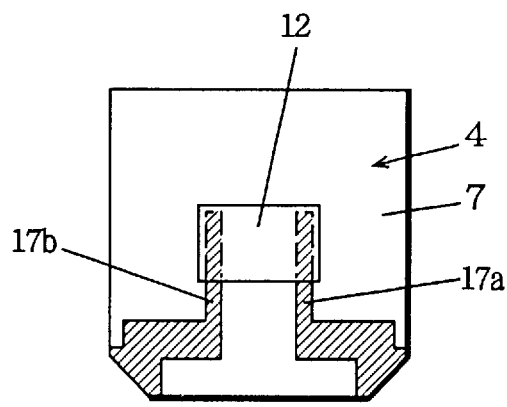
FIG. 3 is a bottom view of an essential part of the gas sensor of which through hole portions have been modified.

A metal oxide semiconductor film 12 such as SnO2 film is provided on the opposite main surface 7 of the substrate 4. The film thickness is, for example, 10 $\mu$m. A pair of electrodes 14a and 14b are connected to the film 12, and these electrodes 14a and 14b are connected to the electrode pads 6c and 6d, respectively, by means of through holes 16 to which conducting layers are provided on the internal walls thereof. As shown in FIG. 3, in place of the through holes 16, conducting layers may be provided at, for example, the edges of the vertexes of the substrate 4. Such an example is shown in FIG. 3. 3 is a new sensor element, and 17a and 17b are new electrodes. The electrodes 10 and 14 may be the same material with the pads 6 or a different material may be used. The film thickness of the electrodes 10 and 14 may be the same with the pads 6 or a different film thickness may be used.

With reference to FIG. 1 and FIG. 2 again, 20 denotes a lead being a precious metal alloy wire. 22 denotes a pin being an external terminal onto which a lead 20 is welded. An alloy wire having a high resistance and a low thermal conductivity, such as Pt—W and Au—Pd—Mo, is used for the leads 20, and Pt—W wire is particularly desirable, which has a low thermal conductivity and can be easily connected to the pads 6. The wire diameter of the leads 20 is, for example, from 20 to 60 $\mu$m, and preferably from 30 to 50 $\mu$m. 24(27?) denotes a thick-film protective layer which is produced by baking a gold paste. The protective layer covers the connections between pads 6 and leads 20. The provision of such protective layers is not needed when the bonding strength between the pads 6 and the leads 20 is satisfactorily high.

Figure 4:
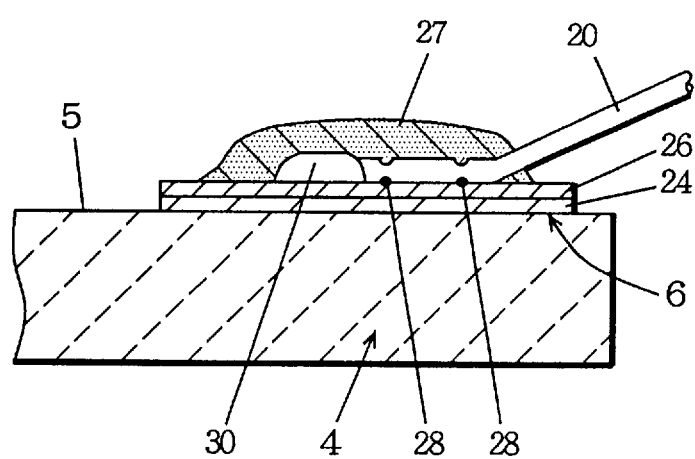
FIG. 4 is a sectional view of an essential part of the embodiment of the gas sensor showing the connection between a pad and a lead.
Figure 5:
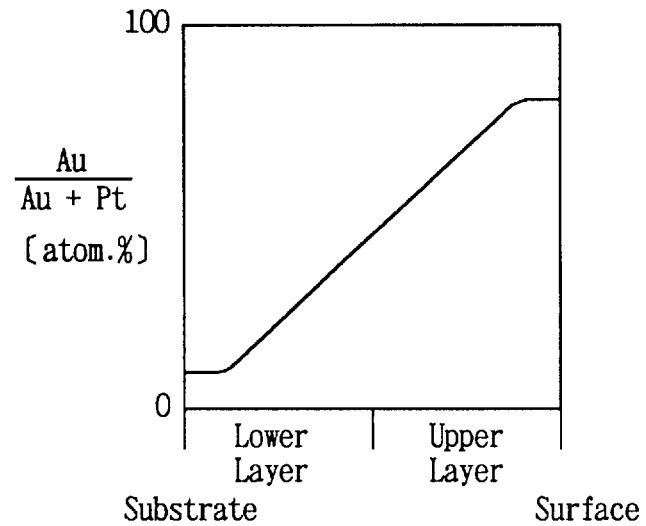
FIG. 5 is a characteristic chart showing the alloying of the pads of the embodiment of the gas sensor.

FIG. 4 shows the connection of the lead 20 to the pad 6. The pad 6 is made of a gold alloy so that the pad 6 has a better adhesion to the substrate 4. FIG. 4 shows an example wherein an upper layer 26 made of pure gold is built up over a lower layer 24 made of pure platinum. However, as shown in FIG. 5, the lower layer 24 and the upper layer 26 are alloyed in the course of baking of the upper layer 26. What is actually obtained is a pad of an alloy of gold and platinum. The inventors, for example, printed a Pt lower layer 24 7 $\mu$m thick and baked at 850° C., and after that, printed a gold upper layer 26 7 $\mu$m and baked at 850° C. The surface of the alloy pad thus obtained did not show the color of gold but silvery white which is the color of an Au—Pt alloy. Thus gold and platinum are alloyed easily. What is actually obtained is a gold-platinum alloy even when two layers of different compositions are printed. This alloying is not limited to the combination of Au—Pt, it occurred with other materials such as Au—Rh and Au—Pd.

Numerals 28 and 28 denote welding portions formed by parallel gap welding. Instead of this, connection between leads 20 and pads 6 may be formed by thermosonic bonding. Or leads 20 may be secured to pads 6 by means of a protective layer 27 without using welding or thermocompression bonding. 30 is a fusing portion of the lead 20. In the case of the embodiment of FIG. 1, two leads are used, and one lead is arranged to connect pads 6a and 6c, then subjected to parallel gap welding. In a similar manner the other lead is arranged to connect pads 6b and 6d and subjected to parallel gap welding. Next, a pair of welding electrodes are made to contact the lead near the fusing portions 30 and 30, and a large current is passed across the pads 6a and 6c or the pads 6b and 6d. As the lead is off the substrate across the pads and there is no escape way for the heat, the lead will be fused and broken. Then a fusing portion 30 will be formed on one end of the lead 20.

The characteristics of the gas sensor thus obtained are described in the following. The substrate 4 is 0.5 mm thick and is rectangular. With reference to FIG. 1, its length in the transverse direction is 1 mm, and the length in the vertical direction is 0.9 mm. The metal oxide semiconductor film 12 was made from SnO2 (film thickness was about 10 $\mu$m), and the baking temperature after printing SnO2 was 700° C. When the pads 6 were formed in one layer and were formed from an alloy from the beginning, the pads 6 were 7 $\mu$m thick. When the pads 6 were formed in two layers, the lower layer from platinum and the upper layer from gold, and they were alloyed together, the platinum layer was 7 $\mu$m thick and the gold layer was 7 $\mu$m thick, hence the pad 6 was 14 $\mu$m thick in total. For leads 20, platinum wire (wire diameter was 40 μm), Pt-ZGS wire (wire diameter was 50 μm; wire wherein ZrO2 is precipitated in grain boundaries of Pt; ZrO2content is about 0.06 wt %), APM wire (wire diameter was 40 μm; Au 55 wt %, Pd 40 wt %, Mo 5 wt %), Pt—W wire (wire diameter was 40 μm; Pt 92 wt %, W 8 wt %) were used. These wire materials were produced by Tanaka Kikinzoku Kogyo. The welding conditions (parallel gap welding) of the wires to the pads 6 were as follows: The welding voltage was 5 V, and the time for passing the welding current was 11 msec. The material of the protective layer 27 was gold paste. The paste was applied and baked at 700° C.

Figure 6:
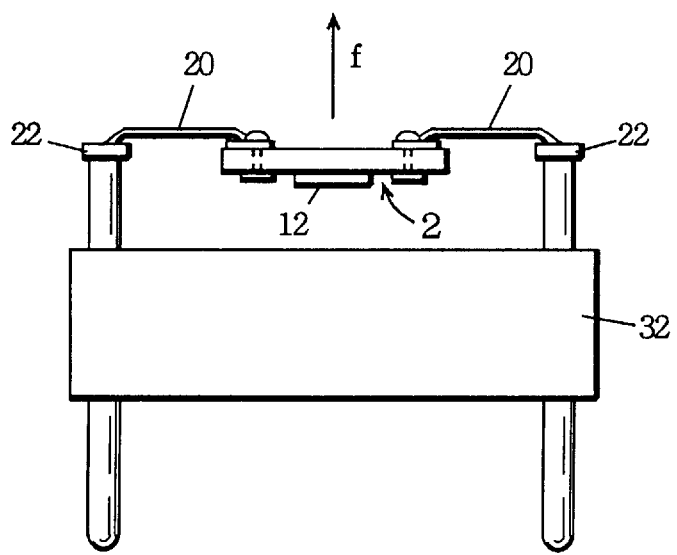
FIG. 6 is a side view of an essential part of the embodiment of the gas sensor.

Regarding the service conditions of the sensor, the temperature change had a period of 30 sec. Of this period, the high temperature range was 10 sec and the low temperature range was 20 sec. The maximum temperature in the high temperature range was about 400° C., and the terminal temperature in the low temperature range was approximately the room temperature. The output of the sensor was sampled, for example, immediately before the completion of the low temperature range. The sensor was subjected to this repeated heat cycle for one year. To measure the bonding strength of the lead 20, as shown in FIG. 6, the sensor element 2 is connected to pins 22, then the sensor element 2 is pulled upward by a special jig. The bonding strength of the lead 20 is expressed by the strength when the lead 20 is disconnected. The positions at which the lead 20 is disconnected were mostly the connection between the pad 6 and the lead 20. In FIG. 6, 32 denotes a base.

Figure 7:
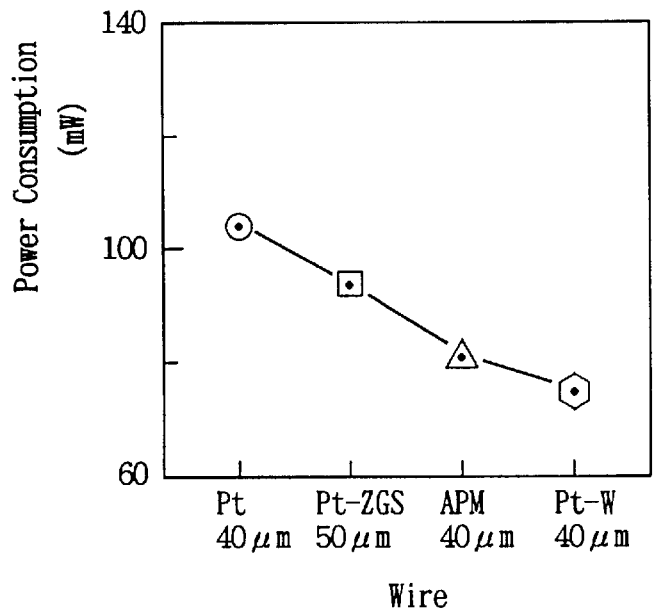
FIG. 7 is a characteristic chart showing the relationship between the kind of lead and the power consumption of the embodiment of the gas sensor.

FIG. 7 shows the change of power consumption (mean power consumption for one period) depending on the kind of leads 20. The power consumption decreases from Pt wire to Pt—W wire. Pt—W wire and APM wire are preferable, and especially Pt—W wire is preferable.

Figure 8:
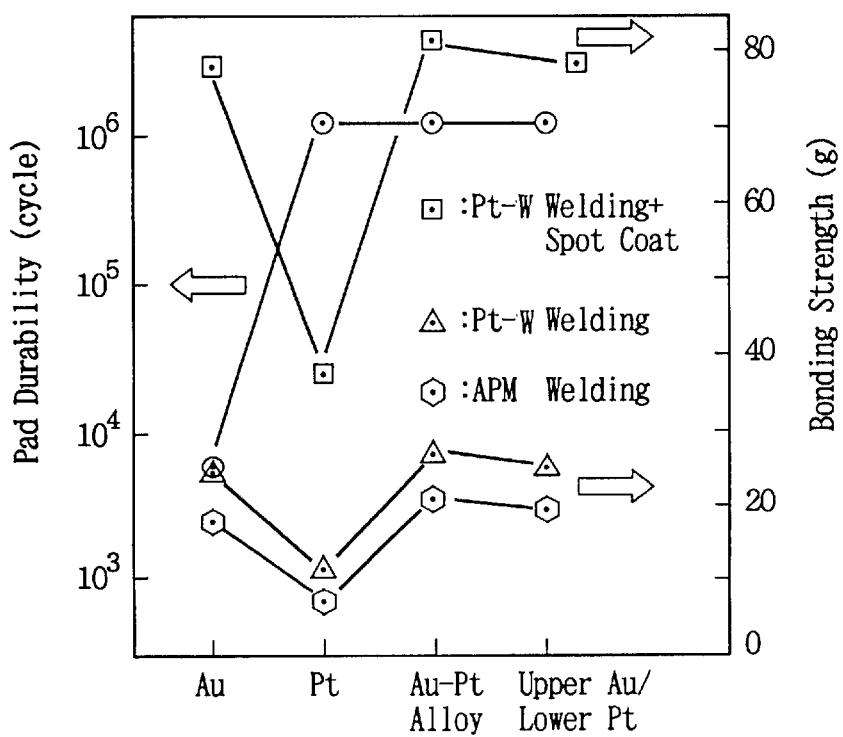
FIG. 8 is a characteristic chart showing the relationship between the kind of thick-film electrode pad and the durability and the relationship between the kind of pad and the bonding strength of lead.

FIG. 8 shows the durability of the pads 6 against heat cycles and the bonding strength of the leads 20. The durability of the pads 60 is indicated by their durability against the number of heat cycles between around 400° C. and around the room temperature in said period of 30 seconds. This value of durability is an average of five sensors. In the case of the pure Au pads, the pad 6 came off the substrate 4 after an average of 6620 cycles. In terms of the service hours of the sensor, this is only 55 hours. On the other hand, the Pt pads and the Au—Pt pads (two kinds: Au—Pt alloy film 7 μm thick; and a gold layer 7 μm was formed over a platinum layer 7 μm then alloyed together) successfully endured the durability test for one year without any peel-off of a pad. The durability test for one year corresponds to 1,050,000 cycles of temperature change.

The kinds of the pads 6 were changed to determine the bonding strengths (overall strengths of the four leads) of the Pt—W wire and the APM wire. For the Pt pads, the bonding strength was about 10 g without the protective layers 27, and about 40 g with the protective layers 27. On the other hand, for the gold pads and the alloy pads such as the gold-platinum pads, the bonding strengths were about 20 g without the protective layers, and about 80 g with the protective layers. This shows that the platinum pads had a deficient bonding strength with leads, and that the gold-platinum alloy pads 6 had an excellent adhesion with the substrate 4 and an increased bonding strength with the leads 20. As is clearly shown in FIG. 8, the Pt—W wire has a greater bonding strength to pads 6 than the APM wire. In addition to the platinum-gold layers, the inventors formed two-layer pads such as Rh—Au and Pd—Au. In all cases, the upper layer was made of gold, and the lower layer was made of Rh, Pd, etc. Both the upper layer and the lower layer were 7 μm thick. In all of these cases, alloying of gold and Rh or Pd took place, and the resulting bonding strengths with the Pt—W wire were about 20 g (without the protective layers 27).

The preceding discussion clearly shows the following:

1) Use of precious alloy wires such as Pt—W and APM reduces the power consumption of the gas sensor.
2) Use of gold alloy pads improves the durability of the gas sensor against temperature changes and assures a high bonding strength of leads to pads.
3) To further enhance the bonding strength of the leads, it is desirable to coat with protective layers 27 after leads 20 are connected to pads 6 by parallel gap welding, thermosonic compression bonding, etc. A preferable material for the protective layers 27 is gold which can be baked at low temperatures, does not give any damage to the metal oxide semiconductor film 12, and can easily bond with pads 6 and leads 20.

FUSING

Figure 9:
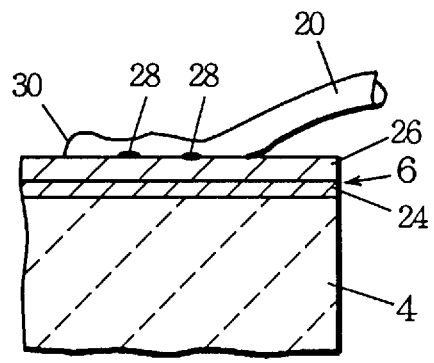
FIG. 9 is a sectional view of an essential part showing a fusing portion of the embodiment of the gas sensor.
Figure 10:
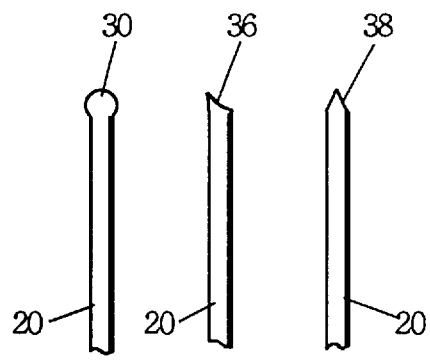
FIG. 10 is a plan view of a fusing portion of the leads in the embodiment of the gas sensor.

FIG. 9 through FIG. 12 show the details of the fusing process. FIG. 9 and FIG. 10 show fusing portions 30 of the lead 20. As shown in FIG. 10, the fusing portion 30 has a shape that differs from those formed by cutting the lead 20 with other methods; the fusing portion 30 is characterized to have roundness. For example, 36 of FIG. 10 shows a shape of the top end of a lead 20 when it is cut off by an edged tool. 38 shows a shape of the top end of a lead 20 when it is strained and torn off.

Figure 2:
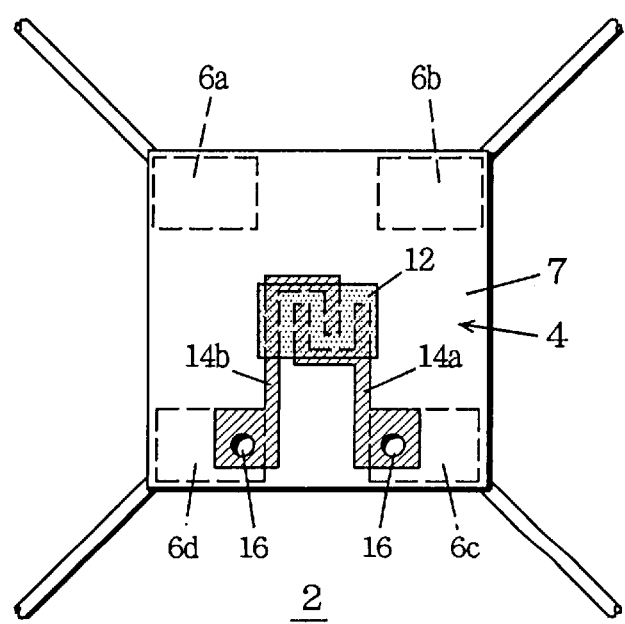
FIG. 2 is a bottom view of the essential part of the embodiment of the gas sensor.
Figure 11:
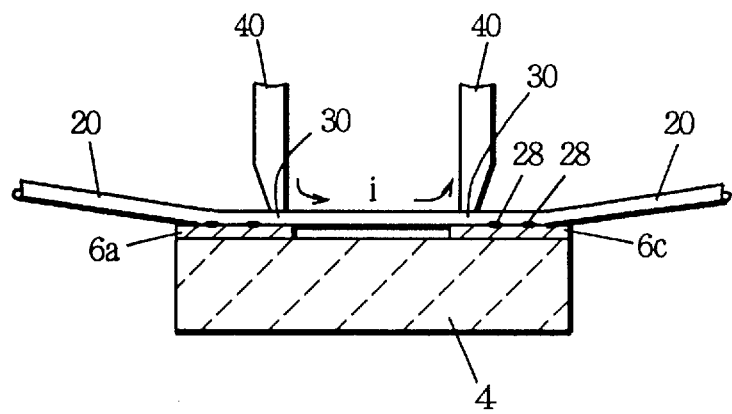
FIG. 11 is a diagram showing the fusing process of a lead in the embodiment.
Figure 12A:
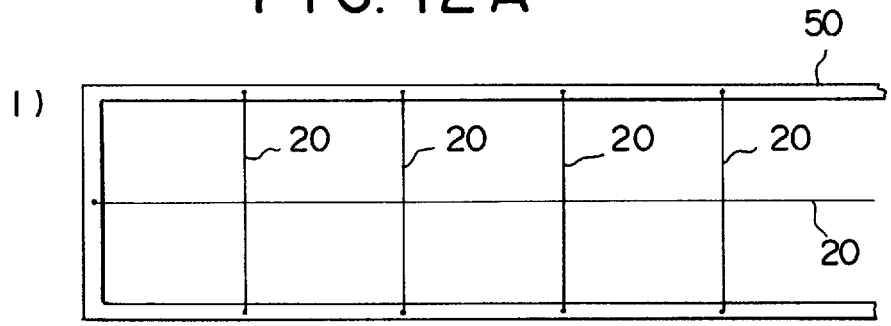
FIG. 12 is a diagram showing the process of connecting leads to the gas sensor in the embodiment.
Figure 12B:
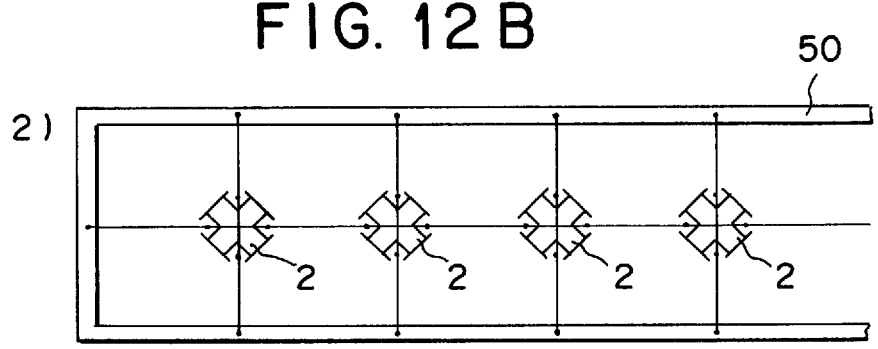
Figure 12C:
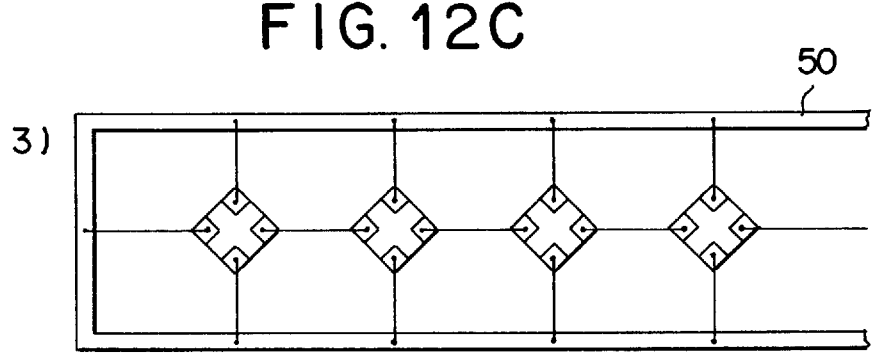
Figure 12D:
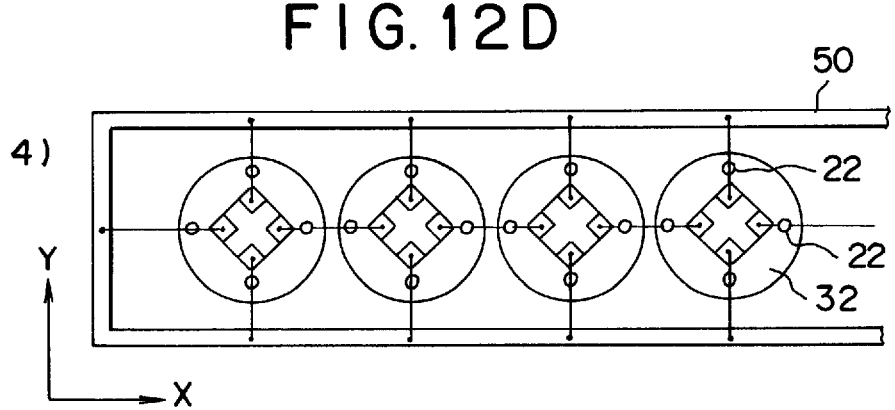

FIG. 11 shows the fusing process. For example, a lead 20 is welded onto pads 6 by parallel gap welding. Then a pair of electrodes 40 and 40 are arranged and a fusing current i is passed. The lead 20 is off the substrate 4 across the pads 6a and 6c, and even if the lead 20 is in contact with the film heater 8, the fusing current will run through the lead 20 since the surface of the film heater 8 is insulated by overglazing. The generated heat will fuse and break the lead 20. FIG. 12 shows a method of connecting leads 20 in the embodiment. FIG. 12 1) shows a metal frame onto which leads 20 are secured by welding, etc. Next, sensor elements 2 are aligned relative to the frame 50 by an appropriate jig. The resulting state is shown in FIG. 12 2). Next, leads 20 are welded to pads 6a through 6d by, for example, parallel gap welding. After that, leads 20 are fused (FIG. 12 3)). Then, gold paste is applied and heated with the entire frame 50 to form protective layers 27. Next, the bases 32 of the gas sensors are aligned, and leads 20 are welded onto pins 22. It is generally difficult to weld leads 20 onto electrode pads 6 and at the same time to cut off leads 20. It, however, is possible to weld leads 20 to pins 22 and at the same time to cut off leads 20. Preferably leads 20 are welded to pins 22 and at the same time leads 20 are cut off (FIG. 12 4)). In this way, the bases 32 become independent of the frame 50, and the mounting of the sensor elements 2 onto the pins 22 is completed. As is clearly shown in FIG. 12 4), the four lead wires change their directions by about 90 degrees, and are virtually parallel to the diagonals of the quadrangle comprising the four pads 6 (the angular deviation of each lead wire from the diagonals is within ±15 degrees). As a result, the sensor elements 2 can resist to forces in both the directions X and Y in FIG. 12; thus the mounting strength of the sensor elements 2 is enhanced.

FIG. 13 shows the gas sensor of the second modification. In this diagram, 70 denotes new sensor elements. 72 is a lead frame, and 74 is a lead thereof. The lead frame 72 is made of a base metal alloy such as SUS316 and iron-chromium-aluminum. For example, the section of the lead 74 is from 20 to 50 μm square. With regard to the sensor element 70, a pair of metal oxide semiconductor films 76 and 78 are arranged on the tail surface of the substrate 4. For example, the metal oxide semiconductor film 76, which is closer to a film heater 8, is used as a metal oxide semiconductor film for detecting methane, and the metal oxide semiconductor film 78, which is distant from the film heater 8, is used as a metal oxide semiconductor film for detecting carbon monoxide. The pad 6*b* is connected both the top and tail surfaces of the substrate by means of a through hole 16, and is used as a pad common to the metal oxide semiconductor films 76 and 78.

A modification of FIG. 13 is similar to the gas sensor of FIG. 1 except base metal angular leads 74 are used as leads, and the sensor element 70 is provided with a pair of metal oxide semiconductor films 76 and 78. For example, pads 6 are all gold alloy pads. These pads have a high adhesion to the substrate 4 and a high bonding strength with leads 74. Moreover, in this modification, sensor elements 70 are aligned relative to the lead frame 72, and leads 74 are welded to the electrode pads 6*a* through 6*d* at four points, and the redundant portions are fused and removed. After that, leads 74 are welded onto pins 22 and at the same time the leads 74 are cut off.

We claim:

1. A gas sensor comprising a heat-resistant insulating substrate:

a metal oxide semiconductor film that changes its electrical resistance according to the presence of gas, a film heater.

a plurality of thick-film electrode pads, each provided on the heat-resistant insulating substrate: and precious metal alloy leads wherein said metal oxide semiconductor film, said film heater and leads are connected to said plurality of thick-film electrode pads, wherein said plurality of thick-film electrode pads are made of a precious metal alloy containing gold, and wherein the connections between said leads and said thick-film electrode pads are covered by thick films of precious metal.

2. A gas sensor as recited in claim 1, wherein the thickness of the electrode pads is in a range of 5–20 μm.

3. A gas sensor as recited in claim 1, wherein said thick-films of precious metal comprise at least one of Au, Au—Pt, Au—Rh.

4. A gas sensor as recited in claim 1 wherein the ends of said leads are fused to said thick-film electrode pads.

5. A gas sensor of claim 4 characterized in that four said thick-film electrode pads are provided and arranged at four vertexes of a quadrangle, one said lead is connected to each of said thick-film electrode pads, and each lead is virtually parallel to a diagonal of said quadrangle that passes the thick-film electrode pad to which said lead is connected.

6. A gas sensor as recited in claim 4, wherein the thickness of the electrode pads is in a range of 5–20 μm.

* * * * *